United States Patent [19]

Grollier et al.

[11] Patent Number: 4,668,508

[45] Date of Patent: May 26, 1987

[54] COMPOSITION FOR THE HAIR, CONTAINING AT LEAST ONE CATIONIC POLYMER, ONE ANIONIC POLYMER, ONE SUGAR AND ONE SALT

[75] Inventors: Jean F. Grollier; Chantal Fourcadier, both of Paris, France

[73] Assignee: L'Oreal, Paris, France

[21] Appl. No.: 578,645

[22] Filed: Feb. 9, 1984

[30] Foreign Application Priority Data

Feb. 9, 1983 [LU] Luxembourg ............................ 84638

[51] Int. Cl.⁴ .......................... A61K 7/06; A61K 7/11
[52] U.S. Cl. ......................................... 424/70; 424/71
[58] Field of Search ............................. 424/70; 421/71

[56] References Cited

U.S. PATENT DOCUMENTS

| | | | |
|---|---|---|---|
| 3,936,402 | 2/1976 | Keegan et al. | 424/49 |
| 3,958,581 | 5/1976 | Abigg et al. | 424/71 |
| 4,364,837 | 12/1982 | Pader | 424/70 |
| 4,371,517 | 2/1983 | Vanlerberge et al. | 424/70 |
| 4,402,977 | 9/1983 | Grollier et al. | 424/71 |
| 4,445,521 | 5/1984 | Grollier et al. | 424/70 |
| 4,488,564 | 12/1984 | Grollier et al. | 424/72 |

FOREIGN PATENT DOCUMENTS

| | | | |
|---|---|---|---|
| 3044754 | 6/1981 | Fed. Rep. of Germany. | |
| 2184890 | 12/1973 | France. | |
| 2883660 | 10/1978 | France. | |
| 2436213 | 4/1980 | France | 424/70 |
| 11799 | of 1913 | United Kingdom | 424/70 |
| 2063671 | 6/1981 | United Kingdom | 424/71 |

OTHER PUBLICATIONS

Sagarin, *Cosmetics Science and Technology*, pp. 162–163, 571, 533–544 (1957).

*Primary Examiner*—Jerome D. Goldberg
*Assistant Examiner*—F. Krosnick
*Attorney, Agent, or Firm*—Fleit, Jacobson, Cohn & Price

[57] ABSTRACT

A composition for the hair, which is intended for use in the treatment of keratinous materials, in particular the hair. This composition contains at least one cationic polymer having a molecular weight of between 500 and 3,000,000, at least one anionic polymer having a molecular weight of between 500 and 3,000,000, at least one sugar and at least one salt in a cosmetically acceptable medium.

12 Claims, No Drawings

COMPOSITION FOR THE HAIR, CONTAINING AT LEAST ONE CATIONIC POLYMER, ONE ANIONIC POLYMER, ONE SUGAR AND ONE SALT

The present invention relates to new compositions based on cationic and anionic polymers, and also containing sugars and salts, which are intended for use in the treatment of keratinous materials, in particular the hair.

The use of compositions based on cationic and anionic polymers is well known in the state of the art and has been described, in particular, in French Pat. No. 2,383,660 of the Applicant Company.

Compositions of this type make it possible, in particular, to achieve ease of comb-out and a pleasant feel with wet hair, and shine, hold and bulk with dried hair.

The use of cationic polymers and anionic polymers with divalent metal salts has already been mentioned elsewhere, in particular in French Pat. No. 2,184,890 of the Applicant Company. Compositions based on cationic and anionic polymers are also known which contain an alkali metal salt and a non-ionic or slightly anionic surface-active agent.

The Applicant Company has discovered that the addition of a sugar and a salt to compositions based on cationic and anionic polymers enables a surprising modification to be made to the rheological characteristics of the polymer films and also to the behaviour of these films towards sebum, compared with the known compositions, resulting, in particular, to an improvement in the bulk and hold of the hair while slowing down the rate at which it becomes greasy again.

The present invention therefore relates to compositions for the hair, containing at least one cationic polymer, at least anionic polymer, at least one sugar and at least one salt.

The invention also relates to the process for the treatment of keratinous materials, in particular for conditioning the hair, using these compositions.

Other subjects of the invention will become apparent on reading the description and the examples which follow.

The compositions for the hair which are intended for the treatment of keratin fibres, in particular the hair, according to the invention, contain at least one cationic polymer and at least one anionic polymer in association with at least one sugar and at least one salt in a cosmetically acceptable medium.

The cationic polymers are polymers of the polyamine, polyaminopolyamide or poly(quaternary ammonium) type in which the amine or ammonium group forms part of the polymer chain or is joined thereto, and which have molecular weights of between 500 and 3,000,000.

The anionic polymers are polymers having a molecular weight of between 500 and 3,000,000 and contain carboxylic or sulphonic acid groups.

The sugars which can be used according to the invention are sugars belonging to the groups consisting of the oses or monosaccharides and their derivatives such as the polyols, and/or to the groups consisting of the holosides, in particular the diholosides.

The salts used according to the invention are inorganic or organic salts, in particular salts of alkali metals, of alkaline earth metals and of divalent or trivalent metal cations.

The cationic polymers, by themselves or in combination with other polymers of this type, are present in proportions of 0.01 to 10% by weight and preferably of 0.05 to 5% by weight, relative to the total weight of the composition. The anionic polymers, by themselves or in combination with other polymers of this type, are present in proportions of 0.01 to 10% and preferably of 0.02 to 5% by weight, relative to the total weight of the composition. The weight ratio of cationic polymers to anionic polymers generally varies between 0.1 and 40 and preferably between 0.1 and 5.

The sugars, by themselves or in combination with other sugars, are present in proportions of 0.1 to 10% and in particular of 0.1 to 3% by weight, relative to the total weight of the composition.

The salts, by themselves or in combination with other salts, are present in proportions of 0.1 to 10% and in particular of 0.1 to 3% by weight, relative to the total weight of the composition.

The weight ratio of sugar to salt generally varies between 0.1 and 2 and in particular between 0.2 and 2.

The cationic polymers which can be used according to the invention are chosen, in particular, from the following polymers:

(1) Vinylpyrrolidone/dialkylaminoalkyl acrylate or methacrylate copolymers (quaternised or unquaternised) such as those sold under the name Gafquat by the Gaf Corp., for example "copolymer 845" and "Gafquat 734 or 755", described in greater detail in particular in French Pat. No. 2,077,143 and French Pat. No. 2,393,573.

(2) Cellulose ether derivatives containing quaternary ammonium groups, such as those described in French Pat. No. 1,492,597 and especially the polymers sold under the name JR, such as JR 125, JR 400 and JR 30 M, and under the name LR, such as LR 400 and LR 30 M, by the Union Carbide Corp., and cationic cellulose derivatives such as CELQUAT L 200 and CELQUAT H 100 sold by National Starch and described in U.S. Pat. No. 4,131,576.

(3) Cationic polysaccharides such as those described in U.S. Pat. Nos. 3,589,978 and 4,031,307, and in particular Jaguar C. 13 S sold by Meyhall.

(4) Cationic polymers chosen from the group comprising (a) polymers containing units of the formula:
—A—Z—A—Z— (I), in which A denotes a radical containing two amine groups, preferably a piperazinyl radical, and Z denotes the symbol B or B'; B and B', which are identical or different, denote a divalent radical which is a straight-chain or branched-chain alkylene radical which contains up to 7 consecutive carbon atoms in the main chain, which is unsubstituted or substituted by hydroxyl groups and which can also contain oxygen, nitrogen and sulphur atoms and 1 to 3 aromatic and/or heterocyclic rings, the oxygen, nitrogen and sulphur atoms being present in the form of ether or thioether, sulphoxide, sulphone, sulphonium, amine, alkylamine, alkenylamine, benzylamine, amine oxide, quaternary ammonium, amide, imide, alcohol, ester and/or urethane groups; these polymers and the process for their preparation are described in French Pat. No. 2,162,025;

(b) polymers containing units of the formula:
—A—$Z_1$—A—$Z_1$— (II), in which A denotes a radical containing two amine groups, preferably a piperazinyl radical, and $Z_1$ denotes the symbol $B_1$ or $B'_1$ and denotes the symbol $B'_1$ at least once; $B_1$ denotes a divalent radical which is a straight-chain or branched-chain alkylene or hydroxyalkylene radical having up to 7 consecutive carbon atoms in the main chain, and $B'_1$ is a divalent radical which is a straight-chain or branched-chain alkylene radical which has up to 7 consecutive carbon atoms in the main chain, which is unsubstituted or substituted by one or more hydroxyl radicals and which is interrupted by one or more nitrogen atoms, the nitrogen atom being substituted by an alkyl chain which is optionally interrupted by an oxygen atom and which optionally contains one or more hydroxyl groups; these polymers and the process for their preparation are described in French Pat. No. 2,280,361;

(c) the alkylation products of the polymers of the formulae (I) and (II) indicated above under (a) and (b) with alkyl or benzyl halides or lower alkyl tosylates or mesylates, and the oxidation products of these polymers.

(5) Optionally alkylated, crosslinked polyaminopolyamides chosen from the group comprising at least one water-soluble crosslinked polymer obtained by crosslinking a polyaminopolyamide (A) prepared by the polycondensation of an acid compound with a polyamine. The acid compound is chosen from: (i) organic dicarboxylic acids, (ii) aliphatic monocarboxylic and dicarboxylic acids with a double bond, (iii) esters of the above-mentioned acids, preferably the esters with lower alkanols having from 1 to 6 carbon atoms, and (iv) mixtures of these compounds. The polyamine is chosen from bis-primary, mono-secondary or bis-secondary polyalkylene-polyamines; 0 to 40 mol % of this polyamine can be replaced by a bis-primary diamine, preferably ethylenediamine, or by a bis-secondary diamine, preferably piperazine, and 0 to 20 mol % can be replaced by hexamethylenediamine. The crosslinking is effected by means of a crosslinking agent (B) chosen from epihalogenohydrins, diepoxides, dianhydrides, unsaturated anhydrides and bis-unsaturated derivatives, in proportions of 0.025 to 0.35 mol of crosslinking agent per amine group of the polyaminopolyamide (A). These polymers and their preparation are described in greater detail in French Pat. No. 2,252,840.

If appropriate, the alkylation is effected with glycidol, ethylene oxide, propylene oxide or acrylamide.

The crosslinked and optionally alkylated polyaminopolyamides do not contain reactive groups, do not have alkylating properties and are chemically stable.

The polyaminopolyamides (A) themselves can also be used according to the invention.

(6) Water-soluble crosslinked polyaminopolyamides obtained by crosslinking a polyaminopolyamide (A) (described above) by means of a crosslinking agent chosen from the group comprising:

(I) compounds of the group comprising (1) bis-halogenohydrins, (2) bis-azetidinium compounds, (3) bis-halogenoacyldiamines and (4) bis(alkyl halides);

(II) oligomers obtained by reacting a compound (a) chosen from the group comprising (1) bis-halogenohydrins, (2) bis-azetidinium compounds, (3) bis-halogenoacyldiamines, (4) bis(alkyl halides), (5) epihalogenohydrins, (6) diepoxides and (7) bis-unsaturated derivatives, with a compound (b) which is a difunctional compound reactive towards the compound (a); and (III) the quaternisation product of a compound chosen from the group comprising the compounds (I) mentioned above and the oligomers (II) and containing one or more tertiary amine groups which can be totally or partially alkylated with an alkylating agent (c) preferably chosen from the group comprising methyl or ethyl chlorides, bromides, iodides, sulphates, mesylates and tosylates, benzyl chloride or bromide, ethylene oxide, propylene oxide and glycidol. The crosslinking is effected by means of 0.025 to 0.35 mol, in particular by means of 0.025 to 0.2 mol and more particularly by means of 0.025 to 0.1 mol of crosslinking agent per amine group of the polyaminopolyamide.

These crosslinking agents and these polymers, together with the process for their preparation, are described in French Pat. No. 2,368,508.

(7) Polyaminopolyamide derivatives resulting from the condensation of polyalkylene-polyamines with polycarboxylic acids, followed by alkylation with difunctional agents. Examples which may be mentioned are adipic acid/dialkylaminohydroxyalkyl-dialkylenetriamine polymers in which the alkyl radical contains from 1 to 4 carbon atoms and preferably denotes methyl, ethyl or propyl, which are described in French Pat. No. 1,583,363.

Amongst these derivatives, there may be mentioned the adipic acid/dimethylaminohydroxypropyl-diethylenetriamine polymers sold under the name Cartaré tine F, $F_4$ or $F_8$ by SANDOZ.

(8) Polymers obtained by reacting a polyalkylenepolyamine containing two primary amine groups and at least one secondary amine group with a dicarboxylic acid chosen from diglycolic acid and saturated aliphatic dicarboxylic acids having from 3 to 8 carbon atoms, the molar ratio of the polyalkylene-polyamine to the dicarboxylic acid being between 0.8:1 and 1.4:1, and the resulting polyaminopolyamide being reacted with epichlorohydrin in a molar ratio of epichlorohydrin to the secondary amine groups of the polyaminopolyamide of between 0.5:1 and 1.8:1; these polymers are mentioned in U.S. Pat. Nos. 3,227,615 and 2,961,347.

The polymers of this type are especially the one sold under the name HERCOSETT 57 by Hercules Incorporated, which has a viscosity of 30 cps in 10% aqueous solution at 25° C., and the one sold under the name PD 170 or DELSETTE 101 by Hercules in the case of the adipic acid epoxypropyl-diethylenetriamine copolymer.

(9) Cyclic polymers having a molecular weight of 20,000 to 3,000,000, such as homopolymers containing, as the main constituent of the chain, units corresponding to the formula (III) or (III'):

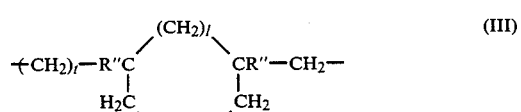

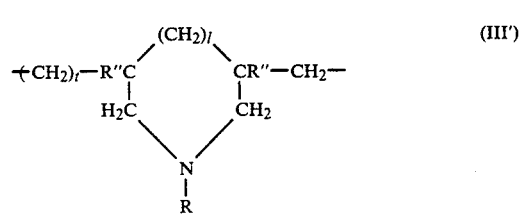

Polymers of this type are described, in particular, in French Pat. Nos. 2,320,330, 2,270,846 and 2,316,271, French Applications 2,336,434 and 2,413,907 and U.S. Pat. Nos. 2,273,780, 2,375,853, 2,388,614, 2,454,547, 3,206,462, 2,261,002 and 2,271,378.

Other polymers of this type are described in U.S. Pat. Nos. 3,874,870, 4,001,432, 3,929,990, 3,966,904, 4,005,193, 4,025,617, 4,025,627, 4,025,653, 4,026,945 and 4,027,020.

(11) Homopolymers or copolymers derived from acrylic or methacrylic acid and containing the unit:

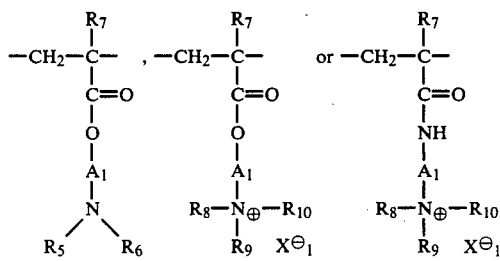

in which $R_7$ is H or $CH_3$, $A_1$ is a linear or branched alkyl group having 1 to 6 carbon atoms or a hydroxyalkyl group having 1 to 4 carbon atoms, $R_8$, $R_9$ and $R_{10}$, which are identical or different, represent an alkyl group having from 1 to 18 carbon atoms or a benzyl group, $R_5$ and $R_6$ represent hydrogen or an alkyl group having from 1 to 6 carbon atoms, and $X_1$ denotes a methosulphate anion or a halide such as chloride or bromide.

The comonomer or comonomers which can be used belong to the family comprising: acrylamide, methacrylamide, diacetone-acrylamide, acrylamide and methacrylamide substituted on the nitrogen by lower alkyls, alkyl esters of acrylic and methacrylic acids, vinylpyrrolidone and vinyl esters.

The following may be mentioned by way of example: the products listed under the names QUATERNIUM 38, 37, 49 and 42 in the Cosmetic Ingredient Dictionary, the acrylamide/beta-methacryloyloxyethyltrimethylammonium methosulphate copolymers sold under the names Reten 205, 210, 220 and 240 by Hercules, the aminoethylacrylate phosphate/acrylate copolymer sold under the name Catrex by National Starch, which has a viscosity of 700 cps in 18% aqueous solution at 25° C., and graft crosslinked cationic copolymers having a molecular weight of 10,000 to 1,000,000 and preferably of 15,000 to 500,000 and resulting from the copolymerisation of:
(a) at least one cosmetic monomer,
(b) dimethylaminoethyl methacrylate,
(c) polyethylene glycol and
(d) a polyunsaturated crosslinking agent,
these copolymers being described in French Pat. No. 2,189,434.

The crosslinking agent is taken from the group comprising: ethylene glycol dimethacrylate, diallyl phthalates, divinylbenzenes, tetraallyloxyethane and polyallylsucroses having from 2 to 5 allyl groups per mol of sucrose.

The cosmetic monomer can be of a very wide variety of types, for example a vinyl ester of an acid having from 2 to 18 carbon atoms, an allyl or methallyl ester of an acid having from 2 to 18 carbon atoms, an acrylate or methacrylate of a saturated alcohol having from 1 to 18 carbon atoms, an alkyl vinyl ether in which the alkyl radical contains from 2 to 18 carbon atoms, an olefine having from 4 to 18 carbon atoms, a vinylic heterocyclic derivative, a dialkyl or N,N-dialkylaminoalkyl maleate in which the alkyl radicals have from 1 to 3 carbon atoms, or the anhydride of an unsaturated acid.

(12) Quaternary vinylpyrrolidone/vinylimidazole polymers such as, for example, luviquat FC 905 sold by B.A.S.F.

(13) Cationic silicone polymers, for example those described in European Applications 17,121 and 17,122, U.S. Pat. No. 4,185,087, Japanese Patent Application No. 80 66,506 and Austrian Patent Application No. 71/01,171, or those mentioned in the CTFA dictionary under the name AMODIMETHICONE, such as the product marketed as a mixture with other ingredients under the name "Dow Corning 929" cationic emulsion.

Other cationic polymers which can be used are polyalkyleneimines, in particular polyethyleneimines, polymers containing vinylpyridine units or vinylpyridinium units in the chain, condensates of polyamines and epichlorohydrin, poly(quanternary ureylene) compounds and chitin derivatives.

The carboxylic acid groups are introduced into the anionic polymers by means of unsaturated monocarboxylic or dicarboxylic acids represented, in particular, by the formula:

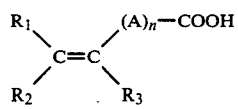

in which n is an integer from 0 to 10, A denotes a methylene group optionally joined to the carbon atom of the unsaturated group, or to the adjacent methylene group in the case where n is greater than 1, via a heteroatom such as oxygen or sulphur, $R_1$ denotes a hydrogen atom or a phenyl or benzyl group, $R_2$ denotes a hydrogen atom or a lower alkyl or carboxyl group and $R_3$ denotes a hydrogen atom, a lower alkyl group, a group —$CH_2$—COOH or a phenyl or benzyl group.

In the abovementioned formula, a lower alkyl radical preferably denotes a group having 1 to 4 carbon atoms, in particular methyl, ethyl or the like.

The preferred anionic polymers used according to the invention are chosen in particular from:

Homopolymers or copolymers of acrylic or methacrylic acid or their salts, in particular the products sold under the name VERSICOL E or K by ALLIED COLLOID and the product sold under the name ULTRAHOLD 8 by CIBA GEIGY, the acrylic acid/acrylamide copolymers sold in the form of their sodium salt under the name RETEN 421, 423 or 425 by HERCULES, the poly(sodium methacrylate) sold under the name DARVAN No. 7 by Van der Bilt, the sodium salts of polyhydroxycarboxylic acids sold under the name HYDAGEN F by HENKEL, and the hydroxycarboxylic polymers sold under the name "POC OS 50-60" by DEGUSSA.

Copolymers of the abovementioned acids with a monoethylenic monomer such as ethylene, vinylbenzene, vinyl or allyl esters or acrylic or methacrylic acid esters, optionally grafted onto a polyalkylene glycol such as polyethylene glycol, and optionally crosslinked, in which 1 and t are equal to 0 or 1 and the sum $l+t=1$, R″ denotes hydrogen or methyl, R and R′ independently of one another denote an alkyl group having from 1 to 22 carbon atoms, a hydroxyalkyl group in which the alkyl group preferably has 1 to 5 carbon atoms, or a lower amidoalkyl group, and R and R′ can denote, together with the nitrogen atom to which they are attached, heterocyclic groups such as piperidinyl or morpholinyl, and also copolymers containing units of the formula III or III′ and units derived from acrylamide or from diacetone-acrylamide, and $Y^-$ is an anion such as bromide, chloride, acetate, borate, citrate, tartrate, bisulphate, bisulphite, sulphate or phosphate.

Amongst the quaternary ammonium polymers of the type defined above, there may be mentioned the dimethyldiallylammonium chloride homopolymer sold under the name MERQUAT 100, which has a molecular weight of less than 100,000, and the dimethyldiallylammonium chloride acrylamide copolymer having a molecular weight of more than 500,000, which is sold under the name MERQUAT 550 by MERCK.

These polymers are described in French Pat. No. 2,080,759 and its Certificate of Addition No. 2,190,406.

(10) Poly(quaternary ammonium) compounds containing repeat units of the formula:

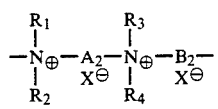

in which $R_1$ and $R_2$, and $R_3$ and $R_4$, which are identical or different, represent aliphatic, alicyclic or arylaliphatic radicals containing at most 20 carbon atoms, or lower hydroxyaliphatic radicals, or alternatively $R_1$ and $R_2$, and $R_3$ and $R_4$, together or separately form, with the nitrogen atoms to which they are attached, heterocycles optionally containing a second heteroatom other than nitrogen, or alternatively $R_1$, $R_2$, $R_3$ and $R_4$ represent a group:

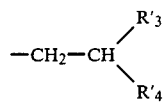

in which R′$_3$ denotes hydrogen or lower alkyl and R′$_4$ denotes one of the following groups:

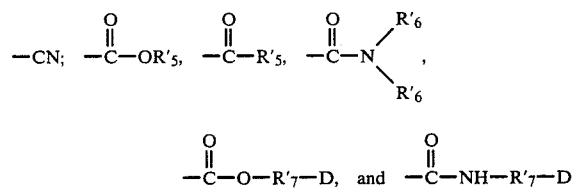

R′$_5$ denoting a lower alkyl group, R′$_6$ denoting hydrogen or a lower alkyl group, R′$_7$ denoting alkylene and D denoting a quaternary ammonium group, $A_2$ and $B_2$ represent polymethylene groups containing from 2 to 20 carbon atoms, which can be linear or branched and saturated or unsaturated and which can contain, inserted in the main chain, one or more aromatic rings such as the group:

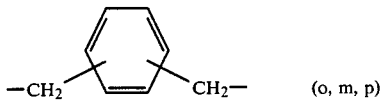

or one or more groups:

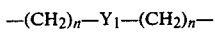

$Y_1$ denoting O, S, SO, SO$_2$, —S—S—,

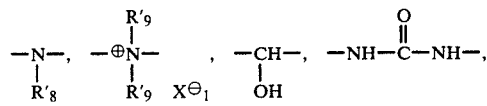

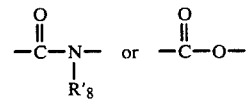

with $X^\ominus_1$ denoting an anion derived from a mineral or organic acid, n being 2 or 3, R′$_8$ denoting hydrogen or a lower alkyl group and R′$_9$ denoting lowr alkyl, or alternatively $A_2$ and $R_1$ and $R_3$ form a piperazine ring with the two nitrogen atoms to which they are attached; moreover, if $A_2$ denotes a linear or branched, saturated or unsaturated alkylene or hydroxyalkylene radical, $B_2$ can also denote a group:

—(CH$_2$)$_n$—CO—D—OC—(CH$_2$)$_2$— in which D denotes:

(a) a glycol radical of the formula —O—Z—O—, in which Z denotes a linear or branched hydrocarbon radical or a group corresponding to the formulae:

or

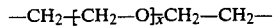

in which x and y denote an integer from 1 to 4, representing a definite and unique degree of polymerisation, or any number from 1 to 4, representing an average degree of polymerisation;

(b) a bis-secondary diamine radical such as a piperazine derivative;

(c) a bis-primary diamine radical of the formula:

—NH—Y—NH—, in which Y denotes a linear or branched hydrocarbon radical or the divalent radical:

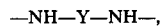

or (d) a ureylene group of the formula —NH—CO—NH—; and $X^\ominus$ is an anion such as chloride or bromide.

These polymers generally have a molecular weight of between 1,000 and 100,000.

such polymers being described, in particular, in French Pat. No. 1,222,944 and German Application No. 2,330,956, and copolymers of this type which contain an optionally N-alkylated and/or hydroxyalkylated acrylamide unit in their chain, such as those described, in particular, in Luxembourg Pat. Nos. 75,370 and 75,371.

Copolymers derived from crotonic acid, such as those containing, in their chain, vinyl acetate or propionate units and, if appropriate, other monomers such as allyl or methallyl esters, a vinyl ether or a vinyl ester of a saturated carboxylic acid with a long hydrocarbon chain, such as those containing at least 5 carbon atoms, or a vinyl, allyl or methallyl ester of an α-cyclic or β-cyclic carboxylic acid, it being possible, if appropriate, for these polymers to be grafted and crosslinked. Polymers of this type are described, inter alia, in French Pat. Nos. 1,222,944, 1,580,545, 2,265,782, 2,265,781, 1,564,110 and 2,439,798. Commercial products falling into this category are the resins 28-29-30, 26-13-14 and 28-13-10 sold by National Starch.

Polymers derived from maleic, fumaric or itaconic acid or anhydride with vinyl esters, vinyl ethers, vinyl halides, phenylvinyl derivatives, acrylic acid and its esters; these polymers can be esterified. Polymers of this type are described, in particular, in U.S. Pat. Nos. 2,047,398, 2,723,248 and 2,102,113 and British Pat. No. 839,805. There may be mentioned, in particular, the polymers sold under the name GANTREZ AN, S or ES by General Aniline or under the name EMA 1325 or 91 by MONSANTO. Other polymers falling into this category are copolymers of maleic, citraconic or itaconic anhydride with an allyl or methallyl ester, which optionally contain an acrylamide or methacrylamide group in their chain and are monoesterified or monoamidified, these copolymers being described in French Pat. Nos. 2,350,834 and 2,357,241 of the Applicant Company.

Polyacrylamides containing carboxylate groups, such as those sold by American Cyanamid under the name CYANAMER A 370.

The acrylic homopolymers are preferably not crosslinked by a polyfunctional agent.

The polymers containing a sulphonic acid group which can be used according to the invention are chosen, in particular, from:

Polystyrenesulphonic acid salts such as the sodium salts sold under the name Flexan 500, which has a molecular weight of about 500,000, or under the name Flexan 130, which has a molecular weight of about 100,000, by National Starch. Compounds of this type are described, in particular, in French Pat. No. 2,198,719.

Alkali metal or alkaline earth metal salts of sulphonic acids derived for lignin, and more particularly calcium or sodium lignosulphonates such as the product sold under the name Marasperse C-21 by American Can Co. and the $C_{10}$-$C_{14}$ products sold by Avébène.

Polyacrylamidesulphonic acid salts such as those mentioned in U.S. Pat. No. 4,128,631, and more particularly the polyacrylamidoethylpropanesulphonic acid sold under the name COSMEDIA POLYMER HSP 1180 by HENKEL.

Polymers containing salified alkylnaphthalenesulphonic acid units, such as the sodium salt sold under the name Darvan No. 1 by Van der Bilt.

Polymers containing at least one vinylsulphonic acid unit, such as, more particularly, polyvinylsulphonates having a molecular weight of between 1,000 and 100,000, and especially their sodium potassium, calcium and ammonium salts, the amine salts such as the alkylamine salts, and the alkanolamine salts, and also copolymers containing at least vinylsulphonic acid groups with one or more cosmetically acceptable comonomers such as unsaturated acids chosen from acrylic and methacrylic acids and their esters, amides such as substituted or unsubstituted acrylamide or methacrylamide, vinyl esters, vinyl ethers and vinylpyrrolidone. These polymers are described more particularly in French Pat. No. 2,238,474 and U.S. Pat. Nos. 2,961,431 and 4,138,477.

It is also possible, according to the invention, to use amphoteric polymers in place of the cationic polymers or alternatively in place of the anionic polymers. In this case, it is compulsory to use amphoteric polymers either with an anionic polymer, in the case where the amphoteric polymer replaces the cationic polymer, or with a cationic polymer, in the case where the amphoteric polymer replaces the anionic polymer.

The amphoteric polymers consist of units A and B randomly distributed in the polymer chain, in which A denotes a unit derived from a monomer containing at least one basic nitrogen atom and B denotes a unit derived from an acid monomer containing one or more carboxylic or sulphonic acid groups, or alternatively A and B can denote groups derived from zwitterionic carboxybetaine monomers; A and B can also denote a cationic polymer chain containing secondary, tertiary or quaternary amine groups, in which at least one of the amine groups carries a carboxylic or sulphonic acid group joined via a hydrocarbon radical, or alternatively A and B form part of a chain of a polymer containing an α,β-dicarboxyethylene unit in which one of the carboxylic acid groups has been reacted with a polyamine containing one or more primary, secondary or tertiary amine groups.

These polymers are described, in particular, in U.S. Pat. No. 3,836,537 and French Pat. No. 1,400,366 and also in French Patent Application No. 79/29,319. It is also possible to use amphoteric polymers of betainised dialkylaminoalkyl acrylate or methacrylate or dialkylaminoalkylacrylamide or dialkylaminoalkylmethacrylamide, containing the following units:

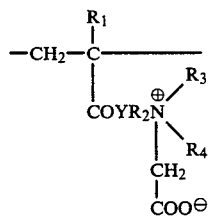

in which $R_1$ denotes a hydrogen atom or a methyl group, $R_2$ denotes an alkylene group having 1 to 4 carbon atoms, Y denotes O or NH and $R_3$ and $R_4$ independently of one another denote hydrogen or alkyl having 1 to 4 carbon atoms, and copolymers with acrylic or methacrylic acid esters containing alkyl radicals having 4 to 24 carbon atoms, and acrylic or methacrylic acid esters containing alkyl radicals having 1 to 3 carbon atoms, and, if appropriate, other monomers such as N-vinylpyrrolidone, acrylamide, hydroxethyl or hydroxpropyl acrylate or methacrylate, acrylonitrile, styrene, chlorostyrene, vinyltoluene, vinyl acetate and the like, which are in themselves known.

The sugars belonging to the groups consisting of the oses or monosaccharides and their derivatives are chosen more particularly from the hexoses such as d-glucose and d-fructose. A polyol which may be mentioned more particularly is mannitol.

Amongst the holosides and in particular the diholosides, there may be mentioned maltose and lactose.

The salts which can be used more particularly in the compositions according to the invention are chosen from salts of sodium, potassium, magnesium, calcium and aluminium. These salts are, in particular, halides such as chlorides, sulphates, nitrates or organic acid salts such as acetates, lactates or gluconates.

A particularly preferred association of the invention consists in using a mixture of sodium chloride, sodium sulphate, potassium sulphate, magnesium sulphate, glucose and fructose. More particularly, it is possible to use an association of sugars and salts comprising 40 to 55% by weight of sodium chloride, 5 to 15% by weight of sodium sulphate, 1 to 4% by weight of potassium sulphate, 1 to 4% by weight of magnesium sulphate, 15 to 25% by weight of glucose and 15 to 25% by weight of fructose.

The compositions for the hair, according to the invention, have a pH varying between 2 and 9 and preferably between 4 and 9. They can be presented in the form of styling lotions, shaping lotions such as setting lotions, blow-drying lotions or lacquers.

The lotions comprise at least one cationic polymer and at least one anionic polymer, at least one sugar and at least one salt as defined above, in aqueous, alcoholic or aqueous-alcoholic solution, together with non-ionic polymers if appropriate. They can be presented in a thickened or gelled form.

These compositions can also be pressurised in aerosol cans, and propellant gases which can be used are carbon dioxide, nitrogen, nitrous oxide, volatile hydrocarbons such as butane, isobutane and propane, and, preferably, the chlorohydrocarbons or fluorohydrocarbons which are well known in the state of the art.

These compositions can also contain any other ingredients normally used in cosmetics, such as perfumes, colourants, preservatives, sequestering agents, thickeners, softeners, synergistic agents or foam stabilisers, sun filters, peptising agents, oils, silicones and acidifying or alkalising agents.

In one embodiment, these compositions can contain cationic surface-active agents such as, more particularly, fatty amine salts such as alkylamine acetates, quaternary ammonium salts such as alkyldimethylbenzylammonium, alkyltrimethylammonium, alkyldimethylhydroxyethylammonium and dimethyldistearylammonium chlorides and bromides, in which the alkyl radicals preferably have between 1 and 22 carbon atoms, quaternary gluconamide halides such as those described in U.S. Pat. No. 3,766,267, cationic protein hydrolysates, quaternary halides of mink oil amide, such as those described in U.S. Pat. No. 4,012,398, quaternary derivatives of dialkylaminopropylamide fatty halogenoalkanoates, such as those described in U.S. Pat. No. 4,038,294, quaternary ammonium derivatives of lanoline fatty acids, such as those described in U.S. Pat. No. 4,069,347, alkylpyridinium salts and imidazoline derivatives.

The process according to the invention is essentially a hair conditioning process which consists in applying a composition such as defined above, in at least one of the steps of the hair treatment, it being possible for this step to be followed by rinsing with water.

The examples which follow are intended to illustrate the invention without implying a limitation.

EXAMPLE 1

The following lotion is prepared:

| | |
|---|---|
| Vinyl acetate/crotonic acid/PEG 20,000 terpolymer (82%/8%/10%) | 0.6 g AI |
| Quaternary polyvinylpyrrolidone copolymer having a molecular weight of 100,000, sold by GENERAL ANILINE under the name GAFQUAT 734 | 0.3 g AI |
| Fructose | 2.0 g |
| CaCl$_2$ | 2.0 g |
| Ethanol q.s. | 50° |
| Water q.s. pH 4.6 | 100 g |

This lotion is applied to the hair, which is dried without intermediate rinsing. The hair has a good hold and does not become greasy again.

EXAMPLE 2

The following composition is prepared:

| | |
|---|---|
| Vinyl acetate/crotonic acid copolymer (90/10) sold by HOECHST under the name ARISTOFLEX A | 1.0 g AI |
| Quaternised cellulose sold by NATIONAL STARCH under the name CELQUAT L200 | 0.5 g AI |
| Ethyl alcohol q.s. | 15° |
| D-Mannose | 1.0 g |
| Magnesium lactate | 2.0 g |
| Colourant, preservative, perfume q.s. 2-Amino-1-methylpropanol q.s. pH 8.6 Water q.s. | 100 g |

EXAMPLE 3

The following composition is prepared:

| | |
|---|---|
| Vinyl acetate/crotonic acid/vinyl neo-decanoate terpolymer sold by NATIONAL STARCH under the name 28/29.30 | 1.0 g AI |
| Quaternary polyvinylpyrrolidone copolymer having a molecular weight of 1,000,000, sold by GENERAL ANILINE under the name GAFQUAT 755 | 0.2 g AI |
| Sodium gluconate | 0.8 g |
| Fructose | 1.0 g |
| Preservative, colourant, perfume q.s. Triethanolamine q.s. pH 8.6 Water q.s. | 100 g |

EXAMPLE 4

The following composition is prepared:

| | |
|---|---|
| Vinyl acetate/crotonic acid copolymer (90/10) sold under the name ARISTOFLEX A by HOECHST | 0.5 g AI |
| Quaternary polyvinylpyrrolidone copolymer having a molecular weight of 100,000, sold by GENERAL ANILINE under the name GAFQUAT 734 | 0.9 g AI |
| Mixture of sugars and salts comprising | |
| Sodium chloride 49% | |
| Sodium sulphate 10% | |
| Potassium sulphate 2.5% | |
| Magnesium sulphate 2% | |

-continued

| | | |
|---|---|---|
| Glucose | 19% | |
| Fructose | 17.5% | 0.5 g |
| Ethyl alcohol q.s. | | 50° |
| Perfume, colourant q.s. | | |
| Lactic acid q.s. pH 5 | | |
| Water q.s. | | 100 g |

EXAMPLE 5

The following composition is prepared:

| | | |
|---|---|---|
| Poly(methyl vinyl ether/maleic anhydride) monobutyl ester sold by GENERAL ANILINE under the name GANTREZ ES 425 | | 0.3 g AI |
| Quaternised cellulose sold by NATIONAL STARCH under the name CELQUAT L200 | | 0.3 g |
| Mixture of sugars and salts comprising | | |
| Sodium chloride | 49% | |
| Sodium sulphate | 10% | |
| Potassium sulphate | 2.5% | |
| Magnesium sulphate | 2% | |
| Glucose | 19% | |
| Fructose | 17.5% | 1.2 g |
| Ethyl alcohol q.s. | | 10° |
| Perfume, colourant, preservative q.s. | | |
| 2-Amino-1-methylpropanol q.s. pH 8 | | |
| Water q.s. | | 100 g |

EXAMPLE 6

The following composition is prepared:

| | | |
|---|---|---|
| Vinyl acetate/crotonic acid copolymer (90/10) sold by HOECHST under the name ARISTOFLEX A | | 1.8 g AI |
| Dimethyldiallylammonium chloride homopolymer of molecular weight <100,000, sold by MERCK under the name MERQUAT 100 | | 0.8 g AI |
| Mixture of sugars and salts comprising | | |
| Sodium chloride | 49% | |
| Sodium sulphate | 10% | |
| Potassium sulphate | 2.5% | |
| Magnesium sulphate | 2% | |
| Glucose | 19% | |
| Fructose | 17.5% | 2.5 g |
| Perfume, colourant, preservative q.s. | | |
| 2-Amino-1-methylpropanol q.s. pH 7.5 | | |
| Water q.s. | | 100 g |

EXAMPLE 7

The following composition is prepared:

| | | |
|---|---|---|
| Adipic acid/diethylenetriamine condensation product crosslinked with epichlorohydrin, according to Example Ia of French Patent 2,252,840 | | 1.0 g AI |
| Vinyl acetate/crotonic acid copolymer (90/10) sold under the name ARISTOFLEX A by HOECHST | | 0.3 g AI |
| Mixture of sugars and salts comprising | | |
| Sodium chloride | 49% | |
| Sodium sulphate | 10% | |
| Potassium sulphate | 2.5% | |
| Magnesium sulphate | 2% | |
| Glucose | 19% | |
| Fructose | 17.5% | 3.5 g |
| Ethyl alcohol q.s. | | 20° |
| Perfume, colourant, preservative q.s. | | |
| Water q.s. | | 100 g |

EXAMPLE 8

The following composition is prepared:

| | |
|---|---|
| Vinyl acetate/crotonic acid/PEG 20,000 terpolymer (82/8/10) | 0.2 g AI |
| Quaternised cellulose sold by UNION CARBIDE under the name JR 400 | 0.6 g AI |
| Ethyl alcohol q.s. | 10° |
| Glucose | 0.5 g |
| Potassium nitrate | 1.2 g |
| Perfume, colourant, preservative q.s. | |
| 2-Amino-1-methylpropanol q.s. pH 7 | |
| Water q.s. | 100 g |

In the various Examples 2 to 8 above, the hair treated with the composition and dried has a good hold and becomes greasy again less quickly.

EXAMPLE 9

The following composition is prepared:

| | |
|---|---|
| Adipic acid/diethylenetriamine polycondensation product crosslinked with the crosslinking agent of the formula: | 3.0 g AI |

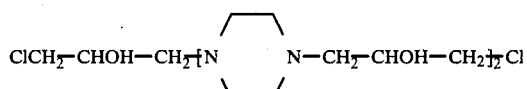

| | |
|---|---|
| described in French Patent 2,368,508 | |
| Mixture of acrylic acid homopolymer and copolymer having an average molecular weight of 3,500, sold as an aqueous solution containing 25% of AI under the name VERSICOL ES by ALLIED COLLOIDS | 3.0 g AI |
| Maltose | 3.0 g |
| Potassium sulphate | 2.7 g |
| Water q.s. | 100 g |
| pH adjusted to 7.5 with hydrochloric acid | |

This composition is applied to washed hair and, after an interval of a few minutes, the hair is rinsed with water and then dried.

EXAMPLE 10

The following composition is prepared:

| | |
|---|---|
| Vinylpyrrolidone/methylvinylimidazolinium chloride copolymer sold as an aqueous solution containing 40% of AI under the name LUVIQUAT FC 905 by BASF | 0.5 g AI |
| Sodium polyvinylsulphonate | 0.5 g AI |
| Maltose | 1.6 g |
| Sodium chloride | 7.0 g |
| Water q.s. | 100 g |
| pH adjusted to 7.4 with sodium hydroxide | |

This composition is applied to the hair like a lotion and the hair is then rinsed with water, after an interval of a few minutes, and dried.

EXAMPLE 11

The following composition is prepared:

| | |
|---|---|
| Octylacrylamide/acrylate/butylaminoethyl methacrylate polymer sold under the name AMPHOMER by NATIONAL STARCH AND CHEMICAL CORPORATION | 0.3 g AI |
| Adipic acid/dimethylaminohydroxypropyl-diethylenetriamine copolymer sold as an | 1.0 g AI |

| | |
|---|---|
| aqueous solution containing 30% of AI under the name CARTARETINE F by SANDOZ | |
| Mannose | 0.5 g |
| Potassium chloride | 3.0 g |
| Water q.s. | 100 g |
| pH adjusted to 8.2 with hydrochloric acid | |

This composition is used as a lotion and its application is followed by rinsing with water.

EXAMPLE 12

The following composition is prepared:

| | |
|---|---|
| Sodium salt of a polyhydroxycarboxylic acid, sold under the name HYDAGEN F by HENKEL | 0.25 g AI |
| Cationic polymer consisting of units of the formula: | |

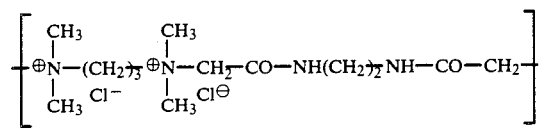

| | |
|---|---|
| described in French Patent 2,413,907 | 2.0 g AI |
| Levulose | 0.4 g |
| Potassium sulphate | 2.0 g |
| Water q.s. | 100 g AI |
| pH adjusted to 7.2 with hydrochloric acid | |

The application of this lotion to the hair is followed by rinsing with water and drying.

EXAMPLE 13

The following composition is prepared:

| | |
|---|---|
| Methacrylic resin of betaine structure, having a molecular weight of between 70,000 and 90,000, sold as a 50% ethanol solution under the name AMPHOSET by MITSUBISHI | 1.0 g AI |
| Ethylene/maleic anhydride copolymer sold under the name EMA 91 by MONSANTO | 0.1 g AI |
| Lactose | 0.6 g |
| Potassium chloride | 3.0 g |
| Water q.s. | 100 g |
| pH adjusted to 8 with hydrochloric acid | |

The application to the hair of the lotion prepared in this way is followed by rinsing with water and drying.

EXAMPLE 14

The following composition is prepared:

| | |
|---|---|
| Cationic polymer consisting of units of the formula: | 0.2 g AI |

$$\left[\begin{array}{cc} CH_3 & CH_3 \\ | & | \\ {}^\oplus N\!-\!(CH_2)_3\!-\!{}^\oplus N\!-\!(CH_2)_6 \\ | \quad Cl^\ominus & | \quad Cl^\ominus \\ CH_3 & CH_3 \end{array}\right]$$

| | |
|---|---|
| described in French Patent 2,270,846 | |
| Methacrylic acid polymer having an average molecular weight of 26,000, sold as an aqueous solution containing 20% of AI under the name VERSICOL K13 by ALLIED COLLOID | 0.5 g AI |
| Maltose | 1.0 g |
| Potassium sulphate | 1.0 g |
| Sodium chloride | 2.0 g |
| Water q.s. | 100 g |
| pH adjusted to 7 with hydrochloric acid | |

The lotion prepared in this way is applied to the hair, which is immediately shaped and dried.

EXAMPLE 15

The following composition is prepared:

| | |
|---|---|
| Polycondensation product of equimolar quantities of piperazine and epichlorohydrin, described in French Patent 2,162,025 | 1.0 g AI |
| Sodium polyvinylsulphonate | 0.5 g AI |
| Lactose | 1.0 g |
| Potassium sulphate | 1.65 g |
| Ethyl alcohol | 2.0 g |
| Water q.s. | 100 g |
| pH adjusted to 8 with hydrochloric acid | |

The hair is impregnated with this lotion, rinsed and then dried.

EXAMPLE 16

The following composition is prepared:

| | |
|---|---|
| Vinylpyrrolidone/methylvinylimidazolinium chloride copolymer sold as an aqueous solution containing 40% of AI under the name LUVIQUAT FC 905 by BASF | 0.25 g AI |
| Copolymer of methyl vinyl ether and maleic acid esterified with butane, sold as an alcoholic solution containing 50% of AI under the name GANTREZ ES 225 by G.A.F. | 0.7 g AI |
| Glucose | 1.0 g |
| Potassium chloride | 3.0 g |
| Ethyl alcohol | 3.0 g |
| Water q.s. | 100 g |
| pH adjusted to 6.5 with sodium hydroxide | |

This composition is packaged in an aerosol device under the following pressurisation conditions:

| | |
|---|---|
| Active composition | 90.0 g |
| Freon 114/12 (43/57) | 10.0 g |
| for | 100 g |

A foam forms as the composition leaves the aerosol device; it is applied to the hair, which is dried and shaped.

EXAMPLE 17

The following composition is prepared:

| | |
|---|---|
| DC 929 cationic silicone emulsion sold by DOW CORNING and composed of amodimethicone, tallow trimonium chloride and nonoxynol-10 according to the definition in the CTFA dictionary (3rd edition) | 1.5 g AI |
| Adipic acid/diethylenetriamine polycondensation product crosslinked with epichlorohydrin in a proportion of 11 mol of epichlorohydrin per 100 secondary amine groups of the polycondensation product, and alkylated with sodium chloroacetate, described in French Patent 2,252,840 | 0.8 g |
| Raffinose | 1.5 g |
| Sodium chloride | 2.0 g |
| Water q.s. | 100 g |
| pH adjusted to 7.5 with hydrochloric acid | |

This composition is in the form of a lotion. The hair treated with this lotion is dried without intermediate rinsing.

EXAMPLE 18

The following composition is prepared:

| | |
|---|---|
| Guar-hydroxypropyltrimethylammonium chloride sold under the name JAGUAR C 13 S by MEYHALL | 0.15 g AI |
| Mixture of acrylic acid homopolymer and copolymer having an average molecular weight of 3,500, sold as an aqueous solution containing 25% of AI under the name VERSICOL F5 by ALLIED COLLOIDS | 0.5 g AI |
| Levulose | 1.0 g |
| Magnesium acetate | 2.0 g |
| Ethyl alcohol | 1.0 g |
| Water q.s. | 100 g |
| pH adjusted to 7.6 with triisopropanolamide | |

This composition is in the form of a lotion. The treated hair is immediately dried and shaped.

EXAMPLE 19

The following composition is prepared:

| | |
|---|---|
| Adipic acid/diethylenetriamine polycondensation product crosslinked with epichlorohydrin in a proportion of 11 mol of epichlorohydrin per 100 secondary amine groups of the polycondensation product, and alkylated with sodium chloroacetate, described in French Patent 2,252,840 | 0.8 g |
| Sodium polystyrenesulphonate sold as a 34% aqueous solution under the name FLEXAN 130 by DELFT NATIONALE | 0.9 g AI |
| Lactose | 2.0 g |
| Sodium chloride | 3.8 g |
| Ethyl alcohol | 5.0 g |
| Water q. s. | 100 g |
| pH adjusted to 7.5 with hydrochloric acid | |

The hair treated with this lotion is dried and shaped.

EXAMPLE 20

The following composition is prepared:

| | |
|---|---|
| Vinylpyrrolidone/methylvinylimidazolinium chloride copolymer sold as an aqueous solution containing 40% of AI under the name LUVIQUAT FC 905 by BASF | 1.0 g |
| Methacrylic acid polymer of MW = 27,000, sold as an aqueous solution containing 30% of AI under the name VERSICOL E$_7$ by ALLIED COLLOIDS | 0.5 g |
| Sodium chloride | 3.0 g |
| Maltose | 2.0 g |
| Copra-dimethylhydroxyethylammonium chloride | 0.5 g |
| Water q.s. | 100 g |
| pH = 6.5, adjusted with hydrochloric acid | |

This composition is in the form of a lotion. It is applied to the hair which, after an interval of a few minutes, is dried and shaped.

We claim:

1. A composition for the cosmetic treatment of hair, which comprises an amount of about 0.01 to 10% by weight of a cationic polymer selected from the group consisting of polyamines, polyamino polyamides, and poly(quaternary ammonium)polymers in which the amine or ammonium group forms a part of the polymer chain or is joined to the polymer chain, said cationic polymer having a molecular weight of between 500 and 3,000,000, an amount of about 0.01 to 10% by weight of an anionic polymer which contains carboxylic or sulfonic acid groups, said anionic polymer having a molecular weight of between 500 and 3,000,000, an amount of about 0.1 to 10% by weight of a sugar selected from the group consisting of the oses or monosaccharides and the holosides; and an amount of about 0.1 to 10% by weight of a salt selected from the group consisting of inorganic or organic salts of alkali metals, alkaline earth metals and divalent or trivalent metal cations, in a cosmetically acceptable medium.

2. A composition according to claim 1, wherein the weight ratio of cationic polymers to anionic polymers varies between 0.1 and 40.

3. A composition according to claim 1 wherein the weight ratio of sugar to salt varies between 0.1 and 2.

4. A composition according to claim 1 in which the cationic polymer is:
   (1) vinylpyrrolidone/dialkylaminoalkyl acrylate or methacrylate copolymers which may or may not be quaternised;
   (2) cellulose ether derivatives containing quaternary ammonium groups, and quaternary cellulose derivatives;
   (3) cationic polysaccharides;
   (4) cationic polymers chosen from polymers containing units of the formula: —A—Z—A—Z— (I), in which A denotes a radical containing two amine groups, preferably a piperazinyl radical, and Z denotes the symbol B or B', B and B', which are identical or different, denoting a linear or branched alkylene radical which is unsubstituted or substituted by hydroxyl groups and which can also contain oxygen, nitrogen and sulphur atoms and 1 to 3 aromatic and/or heterocyclic rings; polymers of the formula: —A—Z$_1$—A—Z$_1$— (II), in which A has the same meaning as above and Z$_1$ denotes the symbol B$_1$ or B'$_1$ and denotes B'$_1$ at least once, B$_1$ being a linear or branched alkylene or hydroxyalkylene radical and B'$_1$ being a linear or branched alkylene radical which is unsubstituted or substituted by one or more hydroxyl radicals and which is interrupted by one or more nitrogen atoms, the nitrogen atom being substituted by an alkyl chain, an alkyl chain interrupted by an oxygen atom, an alkyl chain containing hydroxyl groups, or a alkyl chain interrupted by an oxygen atom and containing hydroxyl groups; and the quaternary ammonium salts and oxidation products of the polymers of the formulae (I) and (II);
   (5) polyaminopolyamides;
   (6) crosslinked polyaminopolyamides chosen from:
   (a) alkylated, crosslinked polyaminopolyamides obtained by crosslinking a polyaminopolyamide prepared by the polycondensation of an acid compound with a polyamine, the crosslinking being effected with a crosslinking agent chosen from epihalogenohydrins, diepoxides, dianhydrides, unsaturated anhydrides and bis-unsaturated derivatives, the crosslinking agent being used in proportions of between 0.025 and 0.35 mol per amine group of the polyaminopolyamide;
   (b) water-soluble crosslinked polyaminopolyamides obtained by crosslinking a polyaminopolyamide defined above with a crosslinking agent chosen from:

(I) bis-halogenohydrins, bis-azetidinium compounds, bis-halogenoacyldiamines and bis(alkyl halides);

(II) oligomers obtained by reacting a compound of group I, or epihalogenohydrins, diepoxides or bis-unsaturated derivatives, with a difunctional compound reactive towards these compounds; and (III) the quaternisation product of a compound of group I, or oligomers of group II, containing tertiary amine groups which can be totally or partially alkylated with an alkylating agent, the crosslinking being effected by means of 0.025 to 0.35 mol of crosslinking agent per amine group of the polyaminopolyamide; and (c) crosslinked polyaminopolyamides obtained by crosslinking a polyaminopolyamide prepared by the polycondensation of an acid compound with a polyamine, the crosslinking being effected with a crosslinking agent chosen from epihalogenohydrins, diepoxides, diahydrides, unsaturated anhydrides and bis-unsaturated derivatives, the crosslinking agent being used in proportions of between 0.025 and 0.35 mol per amine group of the polyamidopolyamide;

(7) polyaminopolyamide derivatives resulting from the condensation of a polyalkylene-polyamine with a polycarboxylic acid, followed by alkylation with difunctional agents;

(8) polymers obtained by reacting a polyalkylene-polyamine containing two primary amine groups and at least one secondary amine group with a dicarboxylic acid selected from the group consisting of diglycolic acid and saturated aliphatic dicarboxylic acids having from 3 to 8 carbon atoms, the molar ratio of the polyalkylene-polyamine to the dicarboxylic acid being between 0.8:1 and 1.4:1, and the resulting polyaminopolyamide being reacted with epichlorohydrin in a molar ratio of epichlorohydrin to the secondary amine groups of the polyaminopolyamide of between 0.5:1 and 1.8:1;

(9) cyclic polymers containing units corresponding to the formula (III) or (III'):

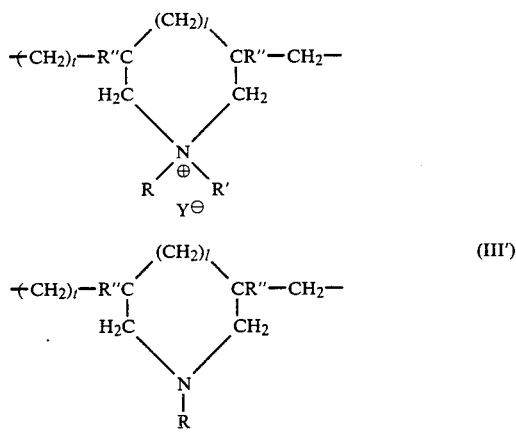

in which e and t are equal to 0 or 1 and $e+t=1$, R''' denotes hydrogen or methyl, R and R' independently of one another denote an alkyl group having 1 to 22 carbon atoms, a hydroxyalkyl group in which the alkyl group preferably has 1 to 5 carbon atoms, or a lower amidoalkyl group, and R and R' can denote, together with the nitrogen atom to which they are attached, heterocyclic groups selected from the group consisting of piperidinyl and morpholinyl, and also copolymers containing units of the formula (III) or (III') and units derived from acrylamide or from diacetone-acrylamide, and $Y^\ominus$ is an anion selected from the group consisting of bromide, chloride, acetate, borate, citrate, tartrate, bisulphate, bisulphite, sulphate and phosphate;

(10) poly(quaternary ammonium) compounds of the formula:

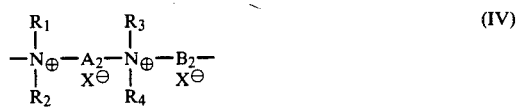

in which $R_1$ and $R_2$, and $R_3$ and $R_4$, which are identical or different, represent aliphatic, alicyclic or arylaliphatic radicals containing at most 20 carbon atoms, or lower hydroxyaliphatic radicals, or alternatively $R_1$ and $R_2$, and $R_3$ and $R_4$, together or separately form, with the nitrogen atoms to which they are attached, heterocycles which may contain a second heteroatom other than nitrogen, or alternatively $R_1$, $R_2$, $R_3$ and $R_4$ represent a group:

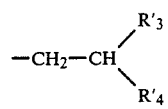

in which $R'_3$ denotes hydrogen or lower alkyl and $R'_4$ denotes:

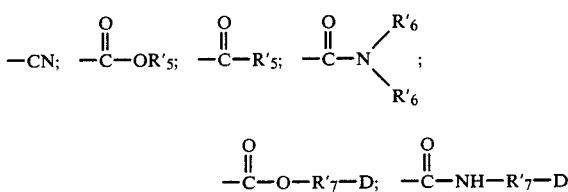

$R'_5$ denoting lower alkyl, $R'_6$ denoting hydrogen or lower alkyl, $R'_7$ denoting alkylene and D denoting a quaternary ammonium group, $A_2$ and $B_2$ can represent polymethylene groups containing from 2 to 20 carbon atoms, which can be linear or branched and saturated or unsaturated and which can contain, inserted in the main chain, one or more aromatic rings selected from the group consisting of:

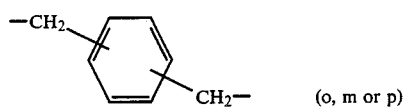

and groups $-(CH_2)_n-Y_1-(Ch_2)_n-$, with $Y_1$ denoting O, S, SO, $SO_2$, $-S-S-$,

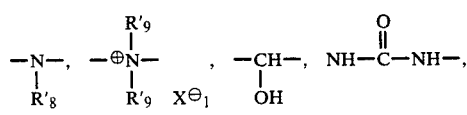

-continued

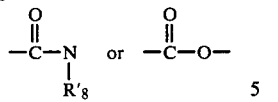

with $X^{\ominus}_1$ denoting an anion derived from a mineral or organic acid, n being 2 or 3, $R'_8$ denoting hydrogen or lower alkyl and $R'_9$ denoting lower alkyl, or alternatively $A_2$ and $R_1$ and $R_3$ form a piperazine ring with the two atoms to which they are attached; moreover, if $A_2$ denotes a linear or branched, saturated or unsaturated alkylene or hydroxyalkylene radical, $B_2$ can also denote a group:

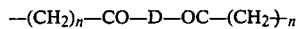
—$(CH_2)_n$—CO—D—OC—$(CH_2)_n$— in which D denotes:
(a) a glycol radical of the formula —O—Z—O—, in which Z denotes a linear or branched hydrocarbon radical or a group corresponding to the formulae:

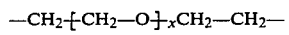
—$CH_2$—$[CH_2$—$O]_x$—$CH_2$—$CH_2$— or

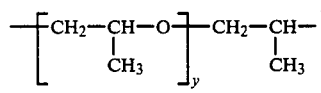

in which x and y denote an integer from 1 to 4;
(b) a bis-secondary diamine radical such as a piperazine derivative;
(c) a bis-primary diamine radical of the formula:

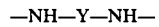
—NH—Y—NH— in which Y denotes a linear or branched hydrocarbon radial or the divalent radical —$CH_2$—$CH_2$—S—S—$CH_2$—$CH_2$—; or
(d) a ureylene group of the formula —NH—CO—NH—; n is such that the molecular weight is generally between 1,000 and 100,000 and $X^{\ominus}$ denotes an anion;

(11) homopolymers or copolymers derived from acrylic or methacrylic acid and containing at least one unit selected from the group consisting of:

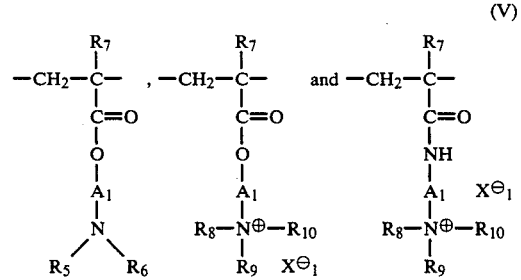
(V)

in which $R_7$ is H or $CH_3$, $A_1$ is a linear or branched alkyl group having 1 to 6 carbon atoms or a hydroxyalkyl group having 1 to 4 carbon atoms, $R_8$, $R_9$ and $R_{10}$, which are identical or different, denote an alkyl group having 1 to 18 carbon atoms or a benzyl group, $R_5$ and $R_6$ denote H or alkyl having 1 to 6 carbon atoms, and $X^{\ominus}_1$ denotes a methosulphate or halide anion;

(12) quaternary vinylpyrrolidone/vinylimidazole copolymers;
(13) cationic silicone polymers;
(14) polyalkyleneimines;
(15) polymers containing vinylpyridine units or vinylpyridinium units in the chain;
(16) condenstes of polyamines and epichlorohydrin; and
(17) poly(quaternary ureylene) compounds.

5. A composition according to claim 1 wherein:
the polymers containing a carboxylic acid group are derived from the unsaturated monocarboxylic or dicarboxylic acids represented by the formula:

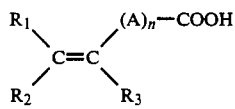

in which n is an integer from 0 to 10, A denotes a methylene group either joined directly to the carbon atom of the unsaturated group, or to an adjacent methylene group if n is greater than 1, via a heteroatom such as osygen or sulphur, $R_1$ denotes a hydrogen atom or a phenyl or benzyl group, $R_2$ denotes a hydrogen atom or a lower alkyl or carboxyl group and $R_3$ denotes a hydrogen atom, a lower alkyl group, a group —$CH_2$—COOH or a phenyl or benzyl group; and
the polymers containing a sulphonic acid group are chosen from:
polystyrenesulphonic acid salts,
alkali metal or alkaline earth metal salts of sulphonic acids derived from lignin,
polyacrylamidesulphonic acid salts,
polymers containing salified alkylnaphthalenesulphonic acid units, and
polymers containing vinylsulphonic acid units.

6. A composition according to claim 1 in which the composition also contains at least one cationic surface-active agent.

7. A composition according to claim 1 presented in the form of an aqueous or alcoholic lotion.

8. A composition according to claim 1 containing as the sugars and salts, a mixture of sodium chloride, sodium sulphate, potassium sulphate, magnesium sulphate, glucose and fructose.

9. A composition according to claim 8, containing 40 to 55% of sodium chloride, 5 to 15% of sodium sulphate, 1 to 4% of potassium sulphate, 1 to 4% of magnesium sulphate, 15 to 25% of glucose and 15 to 25% of fructose.

10. A composition for treating the hair which comprises an amount of about 0.01 to 10% by weight of an amphoteric polymer which consists of units A and B distributed in the polymer chain, in which A denotes a unit derived from a monomer containing at least one basic nitrogen atom and B denotes a unit derived from an acid monomer containing one or more carboxylic or sulphonic acid groups, or alternatively A and B can denote groups derived from zwitterionic carboxybetaine monomers; A and B can also denote a cationic polymer chain containing secondary, tertiary or quaternary amine groups, in which at least one of the amine groups carries a carboxylic or sulphonic acid group joined via a hydrocarbon radical, or A and B form part of a chain of a polymer containing an α,β-dicarboxyethylene unit in which one of the carboxylic acid groups has been reacted with a polyamine containing one or more primary or secondary amine groups; an amount of about 0.01 to 10% by weight of an anionic polymer which contains carboxylic or sulfonic acid groups, said anionic polymer having a molecular weight of between 500 and 3,000,000; an amount of about 0.1 to 10% by weight of a sugar selected from the group consisting of the oses or monosaccharides and the holosides; and an amount of about 0.1 to 10% by weight of a salt selected from the group consisting of inorganic or organic salts of alkali metals, alkaline earth metals and divalent or trivalent metal cations.

11. A composition for treating the hair which comprises an amount of about 0.01 to 10% by weight of an amphoteric polymer which consists of units A and B distributed in the polymer chain, in which A denotes a unit derived from a monomer containing at least one basic nitrogen atom and B denotes a unit derived from an acid monomer containing one or more carboxylic or sulphonic acid groups, or alternatively A and B can denote groups derived from zwitterionic carboxybetaine monomers; A and B can also denote a cationic polymer chain containing secondary, tertiary or quaternary amine groups, in which at least one of the amine groups carries a carboxylic or sulphonic acid group joined via a hydrocarbon radical, or A and B form part of a chain of a polymer containing an α,β-dicarboxyethylene unit in which one of the carboxylic acid groups has been reacted with a polyamine containing one or more primary or secondary amine groups; an amount of about 0.01 to 10% by weight of a cationic polymer selected from the group consisting of polyamines, polyamino polyamides, and poly(quaternary ammonium) polymers in which the amine or ammonium group forms a part of the polymer chain or is joined to the polymer chain, said cationic polymer having a molecular weight of between 500 and 3,000,000; an amount of about 0.1 to 10% by weight of a sugar selected from the group consisting of the oses or monosaccharides and the holosides; and an amount of about 0.1 to 10% by weight of a salt selected from the group consisting of inorganic or organic salts of alkali metals, alkaline earth metals and divalent or trivalent metal cations.

12. A process for treating the hair in order to condition said hair, wherein at least one composition such as defined in claim 1 is applied to said hair.

* * * * *